US011200973B2

(12) United States Patent
Mukherjee et al.

(10) Patent No.: US 11,200,973 B2
(45) Date of Patent: Dec. 14, 2021

(54) SYSTEM, FOR FOOD INTAKE CONTROL

(71) Applicant: International Business Machines Corporation, Armonk, NY (US)

(72) Inventors: Maharaj Mukherjee, Poughkeepsie, NY (US); Monimala Mukherjee, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 289 days.

(21) Appl. No.: 15/401,874

(22) Filed: Jan. 9, 2017

(65) Prior Publication Data
US 2018/0196925 A1    Jul. 12, 2018

(51) Int. Cl.
*G16H 50/30* (2018.01)
*G16H 20/60* (2018.01)
A61B 5/00 (2006.01)

(52) U.S. Cl.
CPC .................................. *G16H 20/60* (2018.01)

(58) Field of Classification Search
CPC .......... G08B 1/08; G16H 20/60; G16H 50/30; G06F 17/30; G06Q 50/12; G06Q 10/60; A61B 5/00; G09G 5/00; G09G 5/02
USPC .............................................. 705/2; 707/709
See application file for complete search history.

(56) References Cited

U.S. PATENT DOCUMENTS

| 6,710,770 | B2 * | 3/2004 | Tomasi | G06F 1/1613 |
| | | | | 345/156 |
| 9,310,891 | B2 * | 4/2016 | Rafii | G06F 3/0304 |
| 9,418,479 | B1 * | 8/2016 | Worley, III | G01B 11/2513 |
| 9,582,913 | B1 * | 2/2017 | Kraft | G06T 11/60 |
| 2002/0049532 | A1 * | 4/2002 | Nakamura | G01C 21/32 |
| | | | | 701/208 |
| 2010/0109876 | A1 * | 5/2010 | Schmid-Schonbein | ...... |
| | | | | G06F 19/00 |
| | | | | 340/573.1 |
| 2012/0179665 | A1 * | 7/2012 | Baarman | G06F 19/3475 |
| | | | | 707/709 |
| 2013/0085345 | A1 * | 4/2013 | Geisner | G06Q 30/00 |
| | | | | 600/300 |

(Continued)

FOREIGN PATENT DOCUMENTS

| CA | 2992950 A1 * | 1/2017 | ............. G06Q 50/12 |
| CN | 104133648 B * | 10/2018 | ......... G06Q 30/0631 |

(Continued)

OTHER PUBLICATIONS

Wang et at.., "PalmType: Using Palms as Keyboards for Smart Glasses", MobileHCI '15: Proceedings of the 17th International Conference on Human-Computer Interaction with Mobile Devices and Services, Aug. 2015 pp. 153-160, (Year: 2015).*

(Continued)

*Primary Examiner* — Jonathan Durant
*Assistant Examiner* — Alaaeldin M Elshaer
(74) *Attorney, Agent, or Firm* — Peter Edwards, Esq.; McGinn I.P. Law Group, PLLC.

(57) ABSTRACT

A food intake control method, system, and computer program product, includes detecting types of food available to a user, categorizing a list of the types of food available to the user based on a harm of a type of food to the user, and administering a nudge to the user to assist the user in avoiding a type of food having the harm.

17 Claims, 4 Drawing Sheets

(56) References Cited

U.S. PATENT DOCUMENTS

| | | | | |
|---|---|---|---|---|
| 2013/0085358 A1* | 4/2013 | Crouther | ............ | A61B 5/14532 600/365 |
| 2013/0157232 A1* | 6/2013 | Ehrenkranz | ........ | G01G 19/4146 434/127 |
| 2014/0018636 A1* | 1/2014 | Contant | ................ | A61B 5/4866 600/301 |
| 2014/0088393 A1* | 3/2014 | Bernstein | ............ | G06F 19/3456 600/365 |
| 2014/0171039 A1* | 6/2014 | Bjontegard | ........... | H04W 4/029 455/414.1 |
| 2014/0172491 A1* | 6/2014 | Karve | ............. | G06Q 10/06315 705/7.25 |
| 2014/0277249 A1* | 9/2014 | Connor | ................ | A61F 5/0026 607/40 |
| 2014/0350369 A1* | 11/2014 | Budiman | ............. | A61B 5/4848 600/365 |
| 2015/0036138 A1* | 2/2015 | Watson | .................. | G01N 21/31 356/402 |
| 2015/0168365 A1* | 6/2015 | Connor | .................. | G01N 33/02 356/51 |
| 2016/0012749 A1* | 1/2016 | Connor | .................... | G09B 5/00 600/13 |
| 2016/0324463 A1* | 11/2016 | Simpson | ................ | A61B 5/742 |
| 2017/0185748 A1* | 6/2017 | Budiman | ............. | A61B 5/7203 |
| 2019/0333634 A1* | 10/2019 | Vleugels | ................ | G16H 40/63 |

FOREIGN PATENT DOCUMENTS

| | | | | |
|---|---|---|---|---|
| WO | WO-2012170584 A1 * | 12/2012 | ........... | A61B 5/0022 |
| WO | WO-2017015612 A1 * | 1/2017 | ............. | G06Q 50/12 |

OTHER PUBLICATIONS

Mel, et al. "The NIST Definition of Cloud Computing". Recommendations of the National Institute of Standards and Technology. Nov. 16, 2015.

* cited by examiner

SYSTEM, FOR FOOD INTAKE CONTROL

BACKGROUND

The present invention relates generally to a food intake control method, and more particularly, but not by way of limitation, to a system, method, and computer program product for detecting a propensity of a user to get tempted to a particular kind of food and assist the user in controlling the intake of the particular kind of food.

There are many situations where an individual should restrict the type and amount of food that they intake because of certain medical conditions or at the advice of their healthcare provider. However, people are always tempted by food when food is present (especially in plenty) around them. For example, someone may attend an office party or a social event where food is all around them. It becomes exceedingly difficult for people to avoid the food when food is aplenty and presented with all its colors and flavors around them. There is a need in the art to help people when they are in such a situation to stay away from the food that ultimately might be harmful for them.

SUMMARY

In an exemplary embodiment, the present invention can provide a computer-implemented food intake control method, the method including detecting types of food available to a user, categorizing a list of the types of food available to the user based on a harm of the type of food to the user, and administering a nudge to the user to assist the user in avoiding the type of food having the harm.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
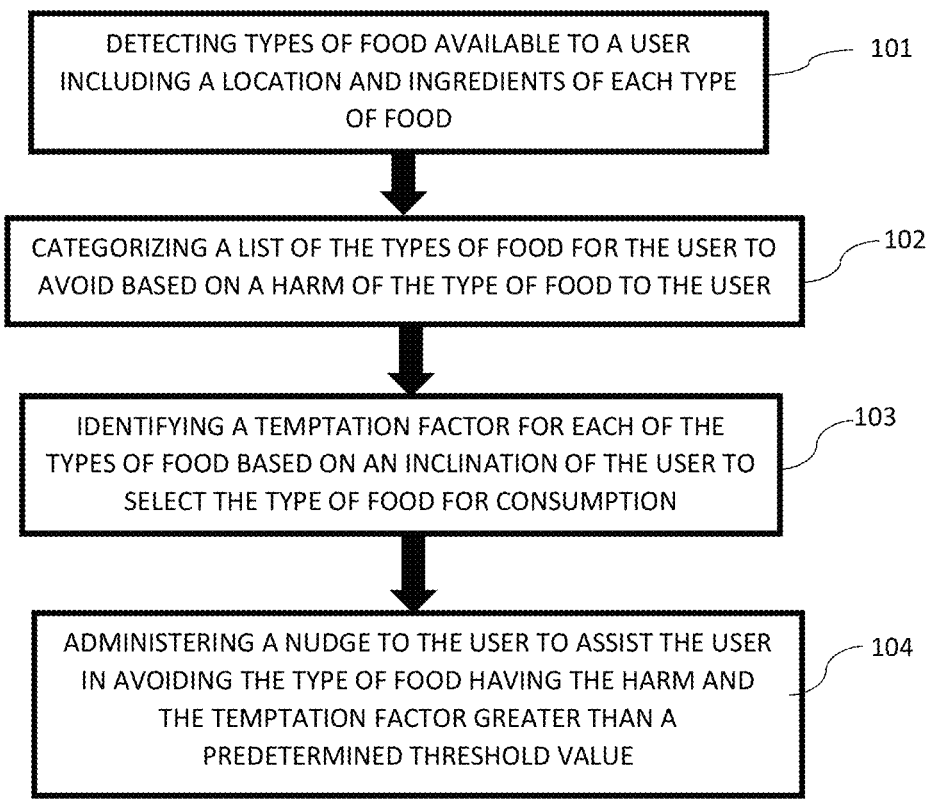
FIG. 1 exemplarily shows a high-level flow chart for a food intake control method 100 according to an embodiment of the present invention.

The invention will now be described with reference to FIGS. 1-4, in which like reference numerals refer to like parts throughout. It is emphasized that, according to common practice, the various features of the drawing are not necessarily to scale. On the contrary, the dimensions of the various features can be arbitrarily expanded or reduced for clarity.

By way of introduction of the example depicted in FIG. 1, an embodiment of a food intake control method 100 according to the present invention can include various steps for detecting a presence of food by visual and/or smell/odor detection to recognize type of the food and based on a knowledge base identifies harmful ingredients in order to nudge a user away from eating harmful foods. By way of introduction of the example depicted in FIG. 2, one or more computers of a computer system 12 according to an embodiment of the present invention can include a memory 28 having instructions stored in a storage system to perform the steps of FIG. 1.

Thus, a food intake control method 100 according to an embodiment of the present invention may act in a more sophisticated, useful and cognitive manner, giving the impression of cognitive mental abilities and processes related to knowledge, attention, memory, judgment and evaluation, reasoning, and advanced computation. In other words, a "cognitive" system can be said to be one that possesses macro-scale properties—perception, goal-oriented behavior, learning/memory and actions generally recognized as cognitive.

Although one or more embodiments may be implemented in a cloud environment 50 (see e.g., FIG. 3), it is nonetheless understood that the present invention can be implemented outside of the cloud environment.

Referring now to FIG. 1, in step 101, a type(s) of food available (e.g., in a proximity of) to the user is detected including a location of the food relative to the user and ingredients for each type of food. The presence of food can be detected using, for example, wearables, cameras, a predetermined input (e.g., such as a menu at a restaurant), etc. by visual, smell, and odor queues. In other words, a device can scan the environment using visual sensor and/or odor detectors and can detect the type of food available to the user, their location and their ingredients.

The location is determined in relation to the user and other foods. That is, a quasi-map of a location of the types of food is plotted in step 101. Also, the ingredients (such as the nutritional facts or a recipe) of each type of food is detected. Thus, foods in a proximity of the user are detected and mapped to their location and the ingredients of the food.

In step 102, a list of the types of food for the user to avoid is categorized based on a harm of each of the foods to the user. That is, the harm is determined according to the specific user, for example, being allergic to an ingredient, having a medical reason to avoid the type of food, etc. The user can have a user profile and the types of food or the ingredients of the food is associated with the user profile to identify the harm (if there is one) of each type of food. In some embodiments, a list of the types foods to avoid is created based on the user's medical history and need. The list can be modified when the user's medical and health situation changes. The list can also be updated based on the ingredients and their potential impact on a person's health.

In some embodiments, the harm of a food to a user can be learned over time. For example, a user may not be aware of an allergy or a type of food that the user should avoid eating. Or, if a user profile indicates that a user became ill when they ate a type of food, a harm is associated with that type of food in the future such that the type of food can be categorized into the list of harmful foods.

It is noted that step 102 can be performed prior to any food being detected or after the food is detected in step 101. For example, prior to any food being detected, a list of harmful foods and ingredients for the user can be created according to a user profile. Then, when foods are detected in step 101 matching the list, each of the harmful foods is categorized in a list for the user to avoid. Alternatively, step 102 may only categorize the harm to the user by identifying the ingredients from the detected foods. Thus, in step 102, a list of harmful foods to a user's health can be categorized.

In step 103, a temptation factor is identified for each of the types of food based on an inclination of the user to select the type of food for consumption. In other words, based on a person's inclination (based on the specific user's history or it could be based on historical data from a general population or cohort of similar people to the user) to choose one type of food over the other, a temptation factor of each kind of food and classifies and orders (i.e., orders the temptation factors) the food based on their temptation impact on the person.

The temptation factor can also be based on external factors and the temptation factors can be adjusted. For example, a temptation factor for ice cream can be increased for a user during the summer as opposed to hot chocolate during the winter. Also, a social presence can be factored into the temptation factor such as a user's temptation to have a glass of wine when home alone is less than in a social setting. Even further, a user's mood or level of exhaustion can adjust the temptation factor. For example, a user may be more likely to select a microwaveable prepared meal over food that takes longer to cook if they are tired.

In step 104, a nudge is administered to the user to assist the user in avoiding the type of food having the harm and/or the type of food in which the temptation factor for the type of food is greater than a predetermined threshold. Based on how a person reacts to what kind of feedback, a nudge is created for all the categories of feedback (e.g., haptic, visual, audio, etc.) and classifies them based on the effectiveness. Since a user may anticipate a kind of feedback as the user gets used to the nudge and thus may become insensitive over time, the nudge can be varied and the intensities occasionally and randomly changed.

A "nudge" described herein includes an action to push (i.e., emotionally push or remind the user to avoid) the user away from an undesirable food.

It is noted that the nudge can be administered by a feedback mechanism such as a wrist band closely connected to the body, a headphone, and a light signal attached to a wearable device or more detailed feedback on a computer eyeglasses such as a pair of google-glasses.

For example, types of nudges can be categorized according to their effectiveness (e.g., effectiveness being determined over time based on the nudge causing the user to avoid the harmful food). Also, an effective nudge now (i.e., currently) may change over time as the user continues to anticipate the nudge. Therefore, the nudge can be changed over time to avoid allowing the user to acclimate to the nudge. In some embodiments, a lowest level of a nudge is administered to the user first (e.g., a vibration at a lowest vibration rate) and over time the vibration intensity increases when the user stops being affected by the vibration.

In other embodiments, the nudge can be visual. For example, the harm to the user can include increased chance of a heart attack when the user consumes foods having high cholesterol. The nudge can be administered as a picture of the user's family. That is, the nudge can include visual feedback in which a combination of different still or moving imagery and/or information on a wearable glass can be administered to the user including images/videos of loved ones, images/videos of a person or self as an impact of eating harmful food, etc. Also, the nudge can include audio feedback that may be administered through an earphone, a blue tooth device, etc. or used in conjunction with the visual feedback (e.g., such as in a video or information). Further, the nudge can include a haptic feedback that can be provided by a wearable device such as a wrist band or something such as being carried within a purse or pocket. The haptic nudge can provide a signal such a vibration, a squeeze, a slight pinch, etc.

The nudge can be administered to the user when the harm is identified with the type of food near the user. That is, the nudge can be administered to the user when the user is in a proximity of a harmful type of food as determined by an ingredient of the food being harmful to the user (or the like). Or, the nudge can be administered based on the temptation factor being greater than a predetermined value. In other words, both a hamburger and a cake may be in the proximity of the user and both have equal harm to the user, but the user never eats cake. However, the user always craves hamburgers. Therefore, the nudge can be administered to help the user avoid the hamburger and the nudge may not be administered for the cake since the user typically does not eat cake. In this manner, the temptation factor can help limit the amount of nudges towards only the types of food that are harmful to the user and that the user typically likes to consume.

In other embodiments, the nudge can be administered only based on the temptation factor irrelevant of whether a food is harmful. Therefore, a user can set up a potential type of food that may not be harmful to the user but that the user would like to avoid as part of their user profile because the user is always tempted to eat this type of food. The temptation factor of the food can be tracked and the nudge can assist the user in avoiding the type of food. Also, the predetermined threshold value can be set according to a user preference such that only "highly" tempted foods are triggered.

In some embodiments, the map of all of the food present in the area can be created based on the location of the food as detected in step 101. This may use multiple cameras as presented on other user devices or use multiple cameras and their locations to create a map of food and where they are present. The locations of the types of food can be used to create a nudge that steers the user away from bad food and towards good food. For example, directional arrows can be administered to the user to steer the user towards a location of good food (i.e., food that is not harmful to the user).

Therefore, steps 101-104 can assist a user in avoiding the consumption of harmful foods by recognizing and categorizing types of food that may be harmful to the user (e.g., harmful foods in a proximity of the user), recognize the user's propensity to be tempted towards a harmful food, and administer a nudge (feedback) to the user to assist the user in avoiding the harmful food and/or the food that the user is tempted to consume.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail) The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 2:
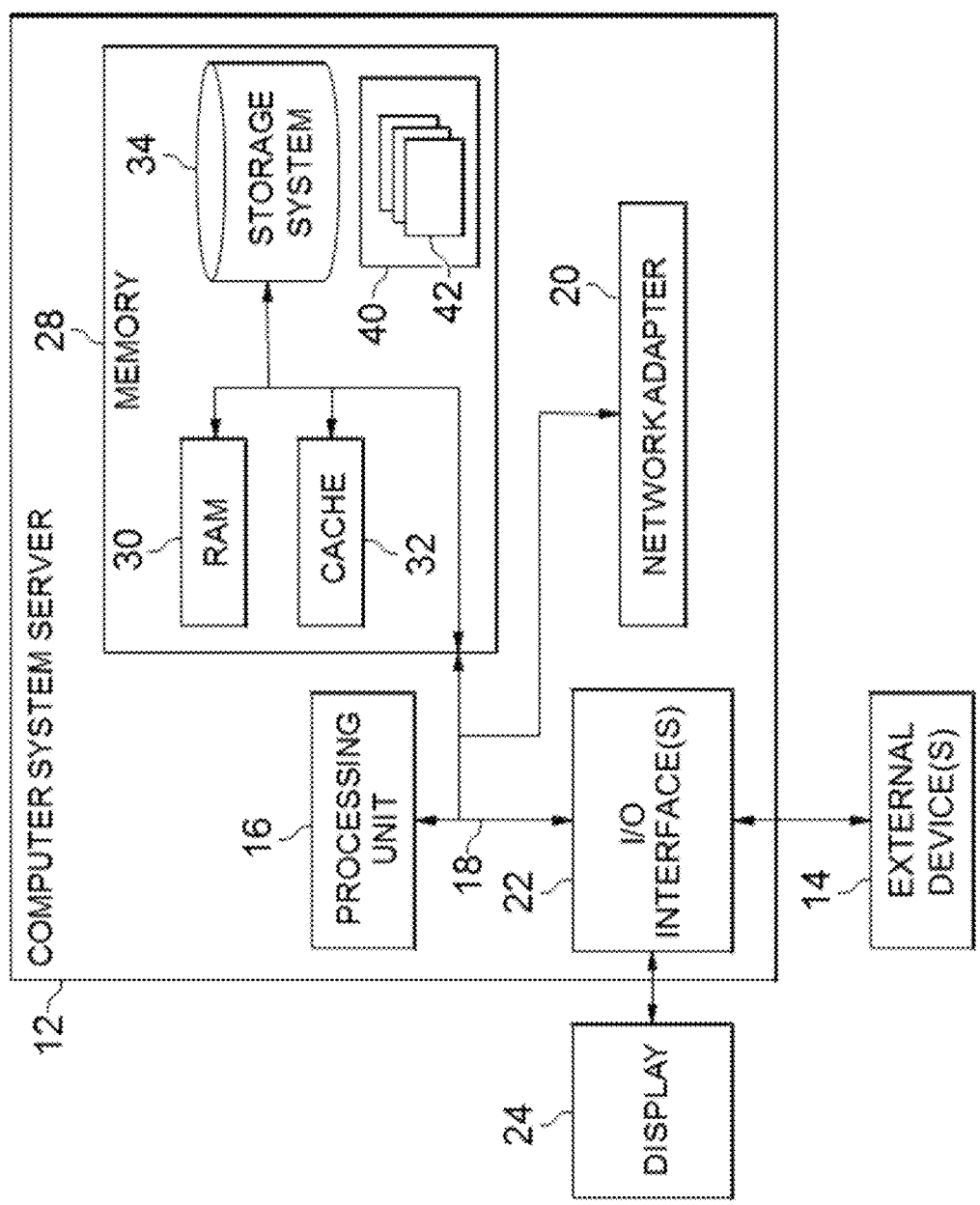
FIG. 2 depicts a cloud-computing node 10 according to an embodiment of the present invention.

Referring now to FIG. 2, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 2, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 3:
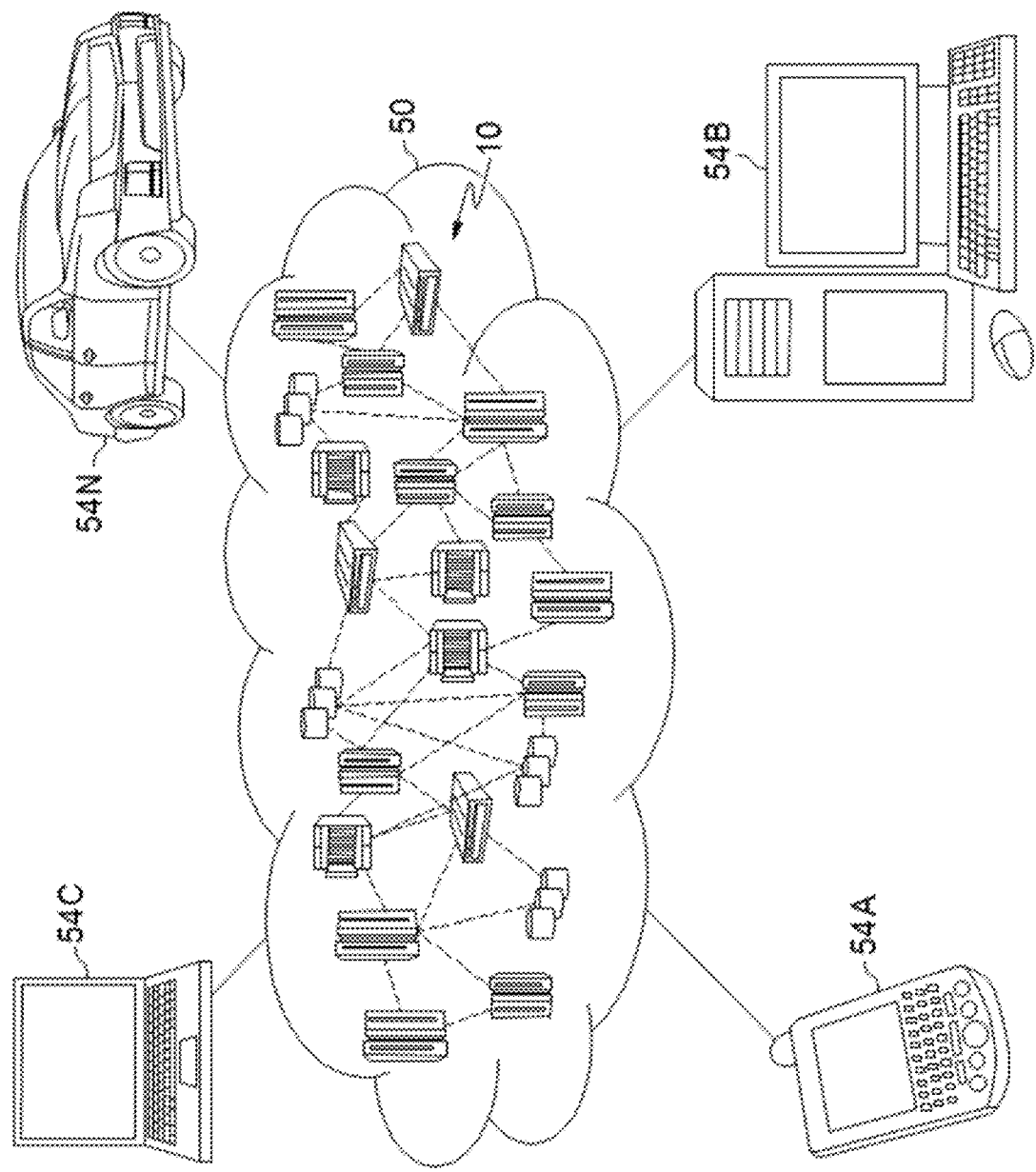
FIG. 3 depicts a cloud-computing environment 50 according to an embodiment of the present invention.

Referring now to FIG. 3, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 3 are intended to be illustrative only and that computing nodes 10 and cloud computing environment 50 can communicate with any type of computerized circuit over any type of network and/or network addressable connection (e.g., using a web browser).

Figure 4:
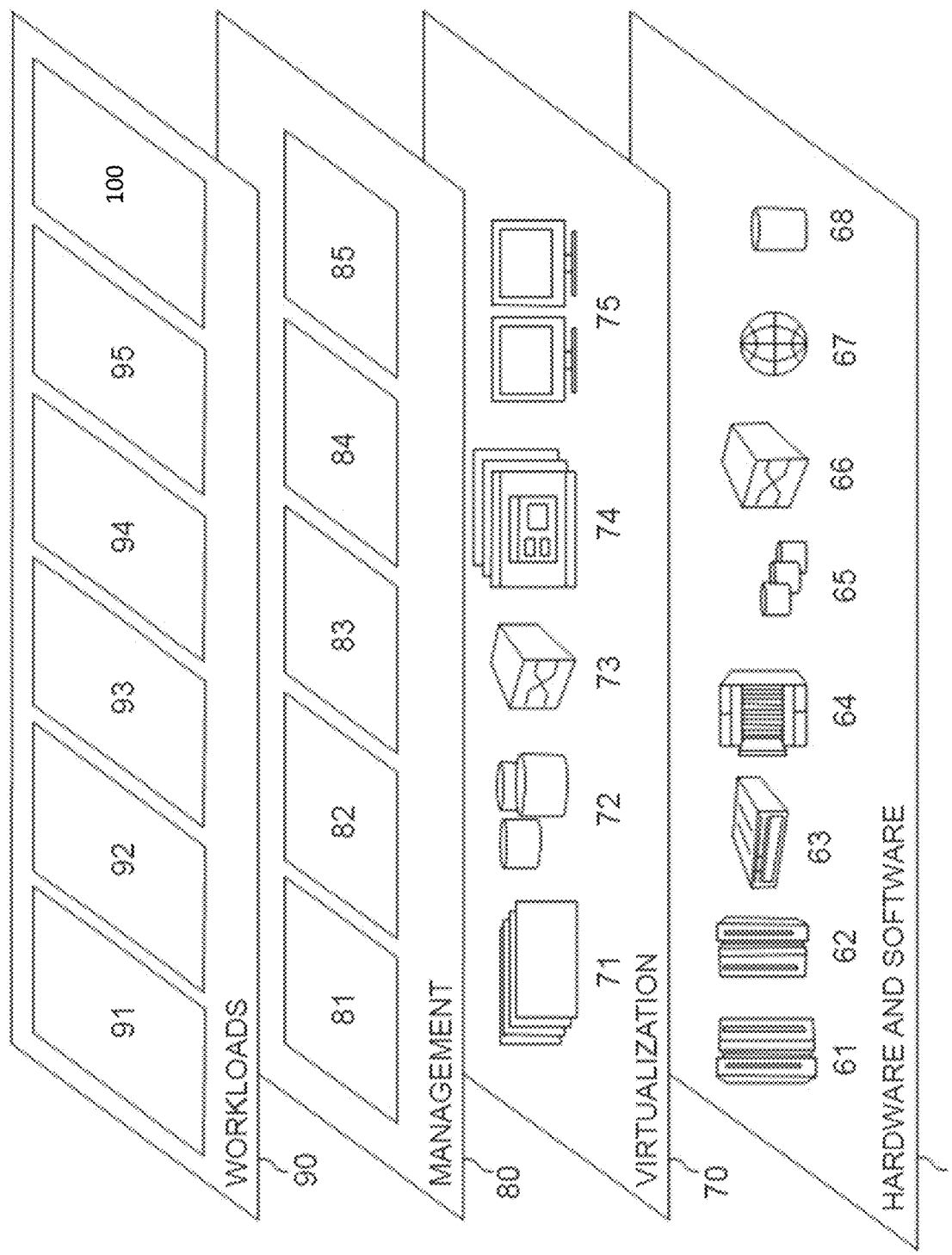
FIG. 4 depicts abstraction model layers according to an embodiment of the present invention.

Referring now to FIG. 4, an exemplary set of functional abstraction layers provided by cloud computing environment 50 (FIG. 43) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and food intake control method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented food intake control method that interacts with a cloud computing environment server, the method comprising:
    detecting types of food available to a user via a first device worn by the user that scans an environment around the user for visual sensors and odor sensors to associate a location and ingredients of the detected types of food, the location being determined in relation to the user and other foods to create a quasi-map that plots the types of food available to the user, the first device comprising a wearable glass, wherein the ingredients of each of the types of foods are also mapped on the quasi-map, the first device communicates with the cloud computing environment server via a cloud on-demand self-service to access a shared pool of configurable computing resources on the cloud computing environment server;
    identifying, using the shared pool of configurable computing resources on the cloud computing environment server, a temptation factor for each of the types of food available to the user based on an inclination of the user to select the type of food for consumption according to a past user behavior in relation to the types of food, the location of the food relative to the user, and in relation to the ingredients in the types of food;
    categorizing, using the shared pool of configurable computing resources on the cloud computing environment server, a list of the types of food available to the user based on a harm of a type of food to the user, the location of the food relative to the user, and the temptation factor, the list of the types of food ranking the harm higher when the temptation factor is greater, and a user profile that stores harms for each of the types of food and associates the harms with the types of food on the list of the types of food, the user profile being dynamic and modified based on a change in a medical history and learned over time according to a reaction of the user to the food on the list; and
    administering, via the first device worn by the user based on a result of the computations performed on the cloud computing environment server, a nudge to the user to assist the user in avoiding a type of food from the list of the types of food having the harm in order to direct the user to a different type of food available to the user at a same time,
    wherein the quasi-map includes all of the detected types of food available and the location of the detected types of food and is created based on a plurality of external cameras and a location of each of the external cameras, the location of the detected types of food plotted on the map being used as a basis of the administering to nudge the user,
    wherein the nudge is created for multiple types of feedback including a haptic feedback, a visual feedback, and an audio feedback,
    wherein, based on a user reaction to the nudge, changing an intensity of a next nudge to increase a likelihood of success of the nudge assisting the user,
    wherein the type of feedback is varied between the multiple types of feedback, at random, with the type of feedback being changed from a first type of the feedback to a second type of the feedback, and
    wherein a visual nudge that is projected on the quasi-map is administered via the first device worn by the user, the visual nudge includes a directional indicator that is displayed on the quasi-map to provide a direction to move away from a first location of a harmful food on the quasi-map in order to steer movement away from the first location and to a second location of a beneficial food on the quasi-map.

2. The computer-implemented method of claim 1, wherein the administering administers the nudge to the user to assist the user in avoiding a type of food in which the temptation factor for the type of food is greater than a predetermined threshold value.

3. The computer-implemented method of claim 1, wherein the list of the types of food that are harmful to the user is based on a user profile.

4. The computer-implemented method of claim 1, wherein the harm of the type of food to the user is learned from the user becoming ill from the consumption of the type of food.

5. The computer-implemented method of claim 1, wherein the temptation factor is determined based on at least one of:
    an external condition including weather;
    a social presence of the user; and
    a mood of the user.

6. The computer-implemented method of claim 1, embodied in a cloud-computing environment.

7. The computer-implemented method of claim 1, wherein the visual sensors include a menu of the types of food available to the user.

8. The computer-implemented method of claim 1, further comprising modifying the list of the types of food based on a learnt food allergy.

9. The computer-implemented method of claim 1, further comprising modifying the list of the types of food over a time period based on an analysis of the impact of the food to the user.

10. The computer-implemented method of claim 1, wherein the type of feedback is varied by randomly alternating between one of the haptic feedback, the visual feedback, and the audio feedback.

11. The computer-implemented method of claim 1, wherein the type of feedback is varied by randomly alternating between the first type of the feedback and the second type of the feedback.

12. The computer-implemented method of claim 1, wherein the type of feedback is varied by alternating between the first type of the feedback to the second type of the feedback when the user ignores the first type of feedback.

13. A computer program product for food intake control, the computer program product comprising a computer readable storage medium having program instructions embodied therewith, the program instructions executable by a computer to cause the computer to perform:
   detecting types of food available to a user via a first device worn by the user that scans an environment around the user for visual sensors and odor sensors to associate a location and ingredients of the detected types of food, the location being determined in relation to the user and other foods to create a quasi-map that plots the types of food available to the user, the first device comprising a wearable glass, wherein the ingredients of each of the types of foods are also mapped on the quasi-map, the first device communicates with the cloud computing environment server via a cloud on-demand self-service to access a shared pool of configurable computing resources on the cloud computing environment server;
   identifying, using the shared pool of configurable computing resources on the cloud computing environment server, a temptation factor for each of the types of food available to the user based on an inclination of the user to select the type of food for consumption according to a past user behavior in relation to the types of food, the location of the food relative to the user, and in relation to the ingredients in the types of food;
   categorizing, using the shared pool of configurable computing resources on the cloud computing environment server, a list of the types of food available to the user based on a harm of a type of food to the user, the location of the food relative to the user, and the temptation factor, the list of the types of food ranking the harm higher when the temptation factor is greater, and a user profile that stores harms for each of the types of food and associates the harms with the types of food on the list of the types of food, the user profile being dynamic and modified based on a change in a medical history and learned over time according to a reaction of the user to the food on the list; and
   administering, via the first device worn by the user based on a result of the computations performed on the cloud computing environment server, a nudge to the user to assist the user in avoiding a type of food from the list of the types of food having the harm in order to direct the user to a different type of food available to the user at a same time,
   wherein the quasi-map includes all of the detected types of food available and the location of the detected types of food and is created based on a plurality of external cameras and a location of each of the external cameras, the location of the detected types of food plotted on the map being used as a basis of the administering to nudge the user,
   wherein the nudge is created for multiple types of feedback including a haptic feedback, a visual feedback, and an audio feedback,
   wherein, based on a user reaction to the nudge, changing an intensity of a next nudge to increase a likelihood of success of the nudge assisting the user,
   wherein the type of feedback is varied between the multiple types of feedback, at random, with the type of feedback being changed from a first type of the feedback to a second type of the feedback, and
   wherein a visual nudge that is projected on the quasi-map is administered via the first device worn by the user, the visual nudge includes a directional indicator that is displayed on the quasi-map to provide a direction to move away from a first location of a harmful food on the quasi-map in order to steer movement away from the first location and to a second location of a beneficial food on the quasi-map.

14. The computer program product of claim 13, wherein the administering administers the nudge to the user to assist the user in avoiding a type of food in which the temptation factor for the type of food is greater than a predetermined threshold value.

15. The computer program product of claim 13, wherein the list of the types of food that are harmful to the user is based on a user profile.

16. A food intake control system, said system comprising:
   a processor; and
   a memory, the memory storing instructions to cause the processor to perform:
      detecting types of food available to a user via a first device worn by the user that scans an environment around the user for visual sensors and odor sensors to associate a location and ingredients of the detected types of food, the location being determined in relation to the user and other foods to create a quasi-map that plots the types of food available to the user, the first device comprising a wearable glass, wherein the ingredients of each of the types of foods are also mapped on the quasi-map, the first device communicates with the cloud computing environment server via a cloud on-demand self-service to access a shared pool of configurable computing resources on the cloud computing environment server;
      identifying, using the shared pool of configurable computing resources on the cloud computing environment server, a temptation factor for each of the types of food available to the user based on an inclination of the user to select the type of food for consumption according to a past user behavior in relation to the types of food, the location of the food relative to the user, and in relation to the ingredients in the types of food;
      categorizing, using the shared pool of configurable computing resources on the cloud computing environment server, a list of the types of food available to the user based on a harm of a type of food to the user, the location of the food relative to the user, and the temptation factor, the list of the types of food ranking the harm higher when the temptation factor is greater, and a user profile that stores harms for each of the types of food and associates the harms with the types of food on the list of the types of food, the user profile being dynamic and modified based on a change in a medical history and learned over time according to a reaction of the user to the food on the list; and
      administering, via the first device worn by the user based on a result of the computations performed on the cloud computing environment server, a nudge to the user to assist the user in avoiding a type of food from the list of the types of food having the harm in order to direct the user to a different type of food available to the user at a same time, wherein the quasi-map includes all of the detected types of food available and the location of the detected types of food and is created based on a plurality of external cameras and a location of each of the external cameras, the location of the detected types of food plotted on the map being used as a basis of the administering to nudge the user, wherein the nudge is created for multiple types of feedback including a haptic feedback, a visual feedback, and an audio feedback, wherein, based on a user reaction to the nudge, changing an intensity of a next nudge to increase a likelihood of success of the nudge assisting the user, wherein the type of feedback is varied between the multiple types of feedback, at random, with the type of feedback being changed from a first type of the feedback to a second type of the feedback, and wherein a visual nudge that is projected on the quasi-map is administered via the first device worn by the user, the visual nudge includes a directional indicator that is displayed on the quasi-map to provide a direction to move away from a first location of a harmful food on the quasi-map in order to steer movement away from the first location and to a second location of a beneficial food on the quasi-map.

17. The system of claim 16, embodied in a cloud-computing environment.

\* \* \* \* \*